(12) United States Patent
Roberts

(10) Patent No.: US 6,841,715 B2
(45) Date of Patent: Jan. 11, 2005

(54) WINDOW DRESSING

(75) Inventor: Jerry H. Roberts, Okemos, MI (US)

(73) Assignee: Tri-State Hospital Supply, Corp., Howell, MI (US)

( * ) Notice: Subject to any disclaimer, the term of this patent is extended or adjusted under 35 U.S.C. 154(b) by 213 days.

(21) Appl. No.: 10/140,427

(22) Filed: May 3, 2002

(65) Prior Publication Data

US 2002/0169405 A1 Nov. 14, 2002

Related U.S. Application Data

(60) Provisional application No. 60/290,076, filed on May 10, 2001.

(51) Int. Cl.$^7$ .......................... A61F 13/00; A61M 25/02
(52) U.S. Cl. ............................. 602/54; 602/42; 602/56; 604/180
(58) Field of Search ................................. 604/174, 179, 604/180; 602/41, 42, 43, 52, 54, 56, 57; 128/888, 889; 206/499, 491

(56) References Cited

U.S. PATENT DOCUMENTS

| | | | | |
|---|---|---|---|---|
| 4,275,721 A | * | 6/1981 | Olson | 604/180 |
| 4,490,141 A | * | 12/1984 | Lacko et al. | 604/180 |
| 4,641,643 A | * | 2/1987 | Greer | 128/888 |
| 5,035,687 A | * | 7/1991 | Sandbank | 604/180 |
| 5,372,589 A | * | 12/1994 | Davis | 604/180 |
| 5,380,294 A | * | 1/1995 | Persson | 604/180 |
| 5,447,492 A | * | 9/1995 | Cartmell et al. | 602/58 |
| 5,520,629 A | * | 5/1996 | Heinecke et al. | 602/57 |
| 5,685,859 A | * | 11/1997 | Kornerup | 604/180 |
| 5,707,348 A | * | 1/1998 | Krogh | 602/41 |
| 5,713,842 A | * | 2/1998 | Kay | 602/57 |
| 5,833,665 A | * | 11/1998 | Bootman et al. | 604/180 |
| 5,885,254 A | * | 3/1999 | Matyas | 604/180 |
| 5,947,931 A | * | 9/1999 | Bierman | 604/180 |
| 5,968,000 A | * | 10/1999 | Harrison et al. | 602/41 |
| 6,071,267 A | * | 6/2000 | Zamierowski | 604/289 |
| 6,124,520 A | * | 9/2000 | Roberts | 602/54 |
| 6,124,521 A | * | 9/2000 | Roberts | 602/54 |
| 6,149,614 A | * | 11/2000 | Dunshee et al. | 602/57 |

* cited by examiner

*Primary Examiner*—Kim M. Lewis
(74) *Attorney, Agent, or Firm*—Fildes & Outland, P.C.

(57) ABSTRACT

A self adherent dermal wound window dressing includes a fabric tape layer having an adhesive skin adhering side and an opposite non-adhesive side. The fabric tape layer has an opening therein to allow viewing therethrough. A semipermeable transparent film layer closes the opening in the fabric tape layer and has an adhesive skin adhering side and an opposite non-adhesive side. The film layer non-adhesive side is adhered on the adhesive side of the fabric layer around the opening such that the fabric layer extends beyond the periphery of the transparent film layer. An absorbent fiber layer having an opening generally corresponding to the opening in the fabric tape layer, is mounted on the adhesive skin adhering side of the transparent film layer such that the openings in the absorbent fiber and fabric tape layers are in alignment and the transparent film layer extends beyond the periphery of the absorbent fiber layer.

11 Claims, 5 Drawing Sheets

WINDOW DRESSING

CROSS REFERENCE TO RELATED APPLICATION

This application claims the benefit of U.S. Provisional Application No. 60/290,076, filed May 10, 2001.

FIELD OF THE INVENTION

This invention relates to dermal wound window dressings for the protection of indwelling catheter access sites, and the visualization and securement of the indwelling catheter and more particularly to a self adherent window dressing having a securement system for edge sealing around the indwelling catheter where the catheter tube extends from under the dressing.

BACKGROUND OF THE INVENTION

It is known in the art relating to dressings for indwelling catheter access sites to use self-adherent protective bandage tape or clear film product alternatives that use non-sensitizing hypoallergenic adhesives to cover all or part of the indwelling catheter access sites. Some dressings combine non-woven tape and absorbent gauze-like materials which have skin-mating surfaces of non-adherent film to reduce the effect of adhesive stripping caused by the dressing removal. The absorbency and bacterial barrier of the pad typically varies minimally from one manufacturer to another, but this type of dressing is least occlusive to moisture vapor.

One known dressing system includes an opaque pad for adhesive placement over an access site and an adhesive strip, for adhesive securement to the skin of a patient under a catheter tube as it emerges from underneath the pad, and between the skin and the pad along the edges of the pad in opposite directions from the tube exit location.

A known transparent type dressing includes a transparent film that does not adhere to the wound site to be viewed. This transparent dressing allows for the placement of a gauze or other absorbing material beneath the transparent film layer over the wound in order to provide absorbency thereby defeating the ability to view the wound site.

Applicant has provided and disclosed in U.S. Pat. Nos. 6,124,520 and 6,124,521, a more sterile, reliable and uniform dressing for a vascular access site, that allows the access site to be viewed without removal of any opaque pad and having a transparent film that adheres to the wound site. This dermal wound window dressing protects an indwelling catheter access site, while providing simultaneous absorbency of moisture, visualization of the skin/cannula exit point and mechanical securement of the indwelling catheter having a securement system for edge sealing around the indwelling catheter where the catheter tube extends from under the dressing. The disclosures of U.S. Pat. Nos. 6,124,520 and 6,124,521 is incorporated by reference herein this application.

Applicant has made further improvements to dermal wound window dressings which improve moisture removal and reduce manufacturing costs.

SUMMARY OF THE INVENTION

The present invention provides a self adherent window dressing having an absorbent pad dressing surrounding a semipermeable transparent cover permitting visual inspection of an indwelling catheter access site; moisture vapor (gaseous) or fluid wicking around the site; and circumfluent absorption of fluid around the site. The window dressing includes a securement system for edge sealing the window dressing around the indwelling catheter where the catheter tube extends from under the dressing next to the skin preventing undesired contaminants from accessing under the dressing from adjacent the catheter tube. The transparent cover adheres to the wound site to be viewed thereby allowing no obstruction to be disposed between the transparent cover viewing area and wound site to be viewed.

More specifically, the present invention is a self adherent dermal wound window dressing for the protection of an indwelling catheter access site, which provides the simultaneous absorption and continuous mitigation of moisture vapor, visualization of the skin/cannula exit point and mechanical securement of the indwelling catheter. The window dressing includes a fabric tape layer having an adhesive skin adhering side and an opposite non-adhesive side. The fabric tape layer has an opening therein to allow viewing therethrough. A semipermeable transparent film layer closes the opening in the fabric tape layer and has an adhesive skin adhering side and an opposite non-adhesive side. The film layer non-adhesive side is adhered on the adhesive side of the fabric layer around the opening such that the fabric layer extends beyond the periphery of the transparent film layer. An absorbent fiber layer having an opening generally corresponding to the opening in the fabric tape layer, is mounted on the adhesive skin adhering side of the transparent film layer such that the openings in the absorbent fiber and fabric tape layers are in alignment and the transparent film layer extends beyond the periphery of the absorbent fiber layer.

In one embodiment the absorbent fiber layer has an opening generally corresponding to the opening in the fabric tape layer and the fiber layer is mounted on the adhesive skin adhering side of the transparent film layer such that said openings in the absorbent fiber and fabric tape layers are in alignment. The absorbent fiber layer shares the same outer periphery shape and size of the transparent film layer. The absorbent fiber layer void of adhesive is thereby held proximal to the skin by the adhesive transparent film layer in the central opening and continually adjoining the skin beyond the absorbent fiber layer by the adhesive fabric tape layer extending beyond the shared outer periphery of the absorbent fiber and adhesive film layers.

Alternatively, the absorbent fiber layer having an opening generally corresponding to the opening in said fabric tape layer and the fiber layer is mounted on the adhesive skin adhering side of the transparent film layer such that the openings in the absorbent fiber and fabric tape layers are in alignment. The outer perimeter of the absorbent fiber layer is unequal in size to the transparent adhesive film layer and extends beyond at least one edge of the film layer concurrently contacting and adhering to the adhesive side of the larger adhesive fabric tape layer.

Herein the absorbent fiber layer void of adhesive is held proximal to the skin by the adhesive transparent film layer in the central opening, and by the larger adhesive fabric tape layer continually adjoining the skin beyond the fiber layer concurrently contacting and adhering to the fiber layer extending beyond at least one edge of the transparent film layer.

In another embodiment of the invention, the self adherent dermal wound window dressing for the protection of an indwelling catheter access site, which provides the simultaneous absorption and continuous mitigation of moisture vapor, visualization of the skin/cannula exit point and mechanical securement of the indwelling catheter, includes a fabric tape layer having an adhesive side and an opposite non-adhesive side; the fabric tape layer has an opening therein to allow viewing therethrough. A semipermeable transparent film layer void of adhesive closes the opening in the fabric tape layer and has a periphery greater than a periphery of the opening and less than a periphery of the fabric tape layer. An absorbent fiber layer void of an adhesive has an opening generally corresponding to the opening in the fabric tape layer. The fiber layer is mounted on the adhesive side of the fabric tape layer such that the openings in the absorbent fiber and fabric tape layers are in alignment and the absorbent fiber layer extends beyond the periphery of the transparent film layer and the fabric tape layer extends beyond the periphery of the absorbent fiber layer.

In yet another embodiment of the self adherent dermal wound window dressing for the protection of an indwelling catheter access site, which provides the simultaneous absorption and continuous mitigation of moisture vapor, visualization of the skin/cannula exit point and mechanical securement of the indwelling catheter, the window dressing includes a semipermeable transparent film layer having an adhesive skin adhering side and an opposite non-adhesive side. An absorbent fiber layer has an opening therein to allow viewing through the opening. The absorbent fiber layer has an adhesive side for adhering the fiber layer to the non-adhesive side of the transparent film layer.

These and other features and advantages of the invention will be more fully understood from the following detailed description of the invention taken together with the accompanying drawings.

DETAILED DESCRIPTION OF THE INVENTION

Figure 1:
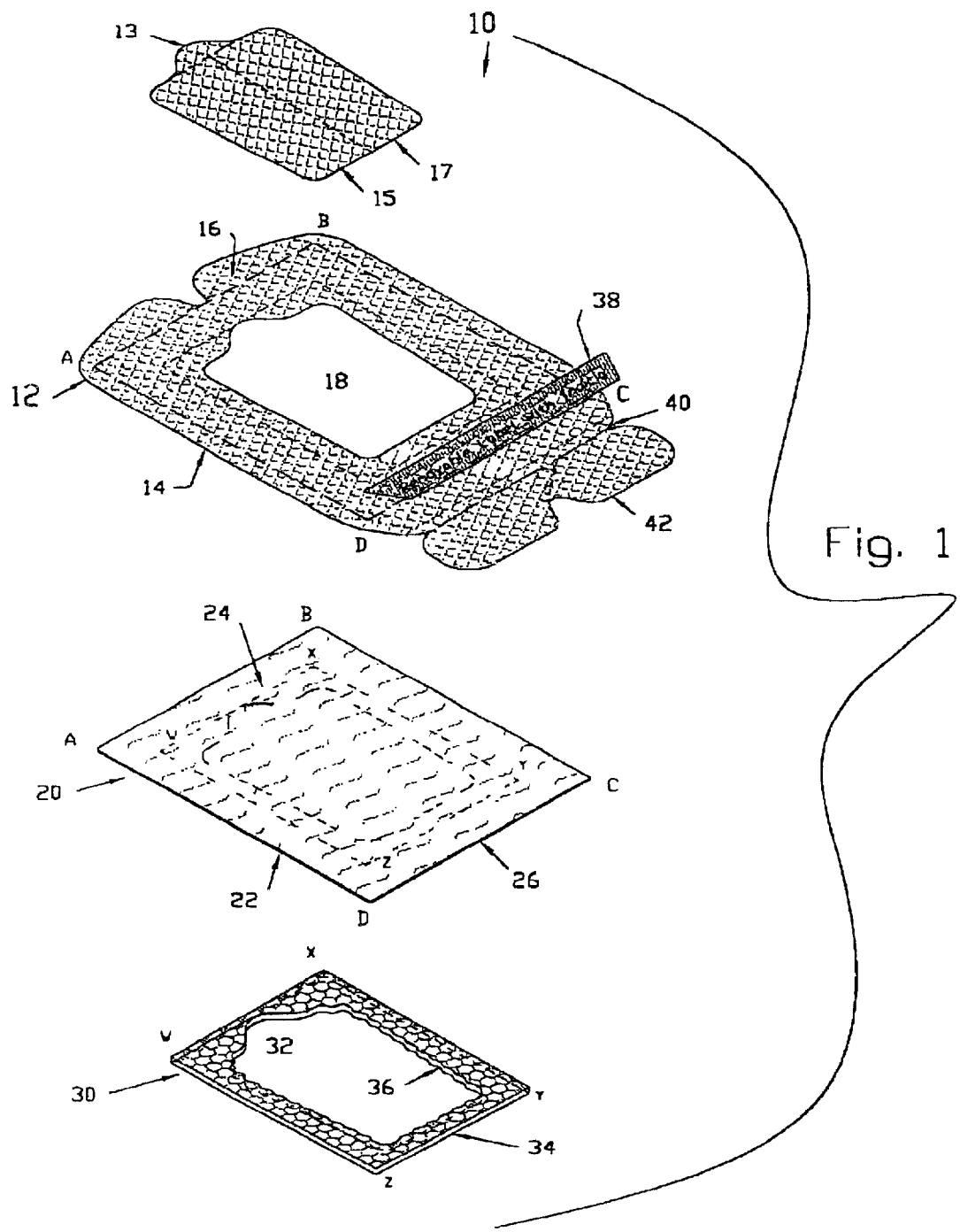
FIG. 1 is an exploded view of one embodiment of a self adherent window dressing of the invention illustrating its layered construction.

Referring now to the drawings in detail, numeral 10 generally indicates a self adherent dermal wound window dressing used on a patient for the protection of a wound or indwelling catheter. As is hereinafter more fully described, the window dressing 10 permits continuous visual inspection of the site and combines a lint-free, highly-absorbent pad that reduces moisture accumulation that heretofore has obscured the site. Furthermore, the dressing 10 possesses high oxygen and moisture permeability, and provides an impermeable barrier to liquids and bacteria.

My related U.S. Pat. Nos. 6,124,520 and 6,124,521, are hereby incorporated by reference.

FIG. 1 illustrates one embodiment of the dressing 10 which includes a fabric tape layer 12 having an adhesive skin adhering side 14 and an opposite non-adhesive side 16. Fabric tape layer 12 comprises a nonwoven polyester material such as DermaMed Coatings Company, LLC rayon/polyester fabric DM-2002 or Tyco fabric part number NW201 having a medical grade adhesive such as an acrylic adhesive applied thereto. Such a fabric tape layer 12 exhibits a water vapor transmission rate exceeding 50 grams per 100 square inches per day, analyzed in accordance with INDA Standard Test IST 70.4 on a Mocon 100K instrument.

The fabric tape layer 12 comprises the top (facing away from the patient) of the dressing and provides a significant portion of the moisture/vapor transmission of the dressing. In a preferred embodiment, the moisture transmission rate is increased when the non-adhesive side 16 has a textured surface, such as a non-planar fabric structure, which enhances the moisture/vapor transmission rate through increased surface area.

The fabric tape layer 12 includes an opening 18 therein to allow viewing therethrough. A semipermeable transparent film layer 20 closes opening 18. Transparent film layer 20 includes an adhesive skin adhering side 22 and an opposite non-adhesive side 24. Transparent film layer 20 comprises a semipermeable polyurethane material such as DermaMed Coatings Company, LLC film DM 4004, 4007 or CT Biomaterials Hydrothane AR25-85A having a medical grade adhesive such as an acrylic adhesive applied thereto. Film layer 20 is preferably a liquid impermeable, bacterial static film which is gas and moisture vapor permeable to provide a high level of moisture vapor and gas (oxygen) exchange, for maintaining normal function of the skin to which it is adhered. The film layer 20 is a moisture permeable material able to exhibit a minimum water vapor transmission rate of 55 grams per 100 square inches per day, analyzed in accordance with INDA Standard Test IST 70.4 on a Mocon 100K instrument.

The film layer non-adhesive side 24 is adhered on the adhesive side 14 of the fabric tape layer 12 around the opening 18 and the fabric tape layer extends beyond the periphery 26 of the transparent film layer.

An absorbent fiber layer 30 comprises the bottom (against a patient's skin) layer of dressing 10 and has an opening 32 therein generally corresponding to the opening in the fabric tape layer 12. Absorbent fiber layer 30 comprises a nonwoven polyester fabric that provides circumfluent moisture absorption around the opening 32 keeping the viewing area of the film layer 20 clear and dry. The fiber layer 30 is mounted on the adhesive, skin adhering side 22 of the film layer 20 such that the openings 18 and 32 in the fiber and tape layers are in alignment and the film layer extends beyond the periphery 34 of the absorbent fiber layer.

With continued reference to FIG. 1, opening 32 in the absorbent layer 30 has a scalloped or undulating edge 36 around opening 32 which is preferable to a straight cut edge, although a straight cut shaped edge is within the scope of the invention. The scalloped cut edge 36 provides a greater surface area than a straight cut edge which translates into increased moisture/vapor transmission as the scalloped edge draws and wicks moisture and disposes of it by communicating such moisture outwardly through the absorbent layer 30. The scalloped or undulating edge 36 also increases the ability of the dressing 10 to conform to and lay down on the contoured surfaces of a patient.

A label portion 38 is removably mounted along an outside edge 40 of the fabric tape layer 12. The label portion also includes an adhesive side and may include indicia on the non-adhesive top side. Preferably the label portion 38 is an extension of the fabric tape layer 12 perforated along the edge 40 for easy removal. The fabric tape layer 12 has an opening 18 therein to allow viewing therethrough; the central cut portion 13 of the tape layer 12 is then typically removed and discarded in the manufacturing process. One embodiment of the current invention allows this removable central cut portion 13 of otherwise discarded fabric tape 12 to remain adhered to the protective release backing 42 on which it is supplied. The removable central cut portion 13 is held in place attached only at the periphery of the opening 18 of the fabric tape layer 12 and is then capable of being removed easily from the opening 18 by the end user and allows for the viewing through the opening 18. The removable central cut portion 13 of fabric tape 12 is protected on the adhesive side 14 by a release backing 42 generally corresponding in size and shape to the removable central cut portion 13 of the fabric tape layer and is therefor valuable as a portion of fabric tape 12. This removable central cut portion 13 of fabric tape 12 may be subdivided into multiple smaller portions 15 and 17 of useful fabric tape strips by the same manufacturing process of cutting the opening area 18 that would otherwise cut through, remove and discard the central cut portion 13 in the process of manufacturing. In this embodiment the removable central cut portion 13 is reclaimed for use as an adjunct and ancillary portion of fabric tape 12, or multiple smaller portions 15 and 17 of tape strips by subdivision of the fabric tape layer 12 making it useful for further securement of the catheter exiting beneath the edge of the dressing 10. The release backing 42 is removed prior to dressing 10 application.

The non-adhesive side 16 of the fabric tape layer 12 may be coated with a water repellant, for example a flourochemical treatment such as is available from Precision Fabrics Group to provide repellency to water and other liquids. The non-adhesive side 16 of the fabric tape layer 12 would exhibit a resistance to water (Hydrostatic Pressure Test) as analyzed in accordance with INDA Standard IST 80.6 and provide a surface that is repellant to liquids yet still allows the adherence of adhesive tapes to stick to the non-adhesive side 16 of the fabric tape layer 12. This treatment would provide increased resistance to water and increased adhesive holding strength to the skin when a patient wearing the dressing may be in the shower or in the act of bathing or other environments of high humidity such as are common in many seasonal warm and tropical climates.

Figure 2:
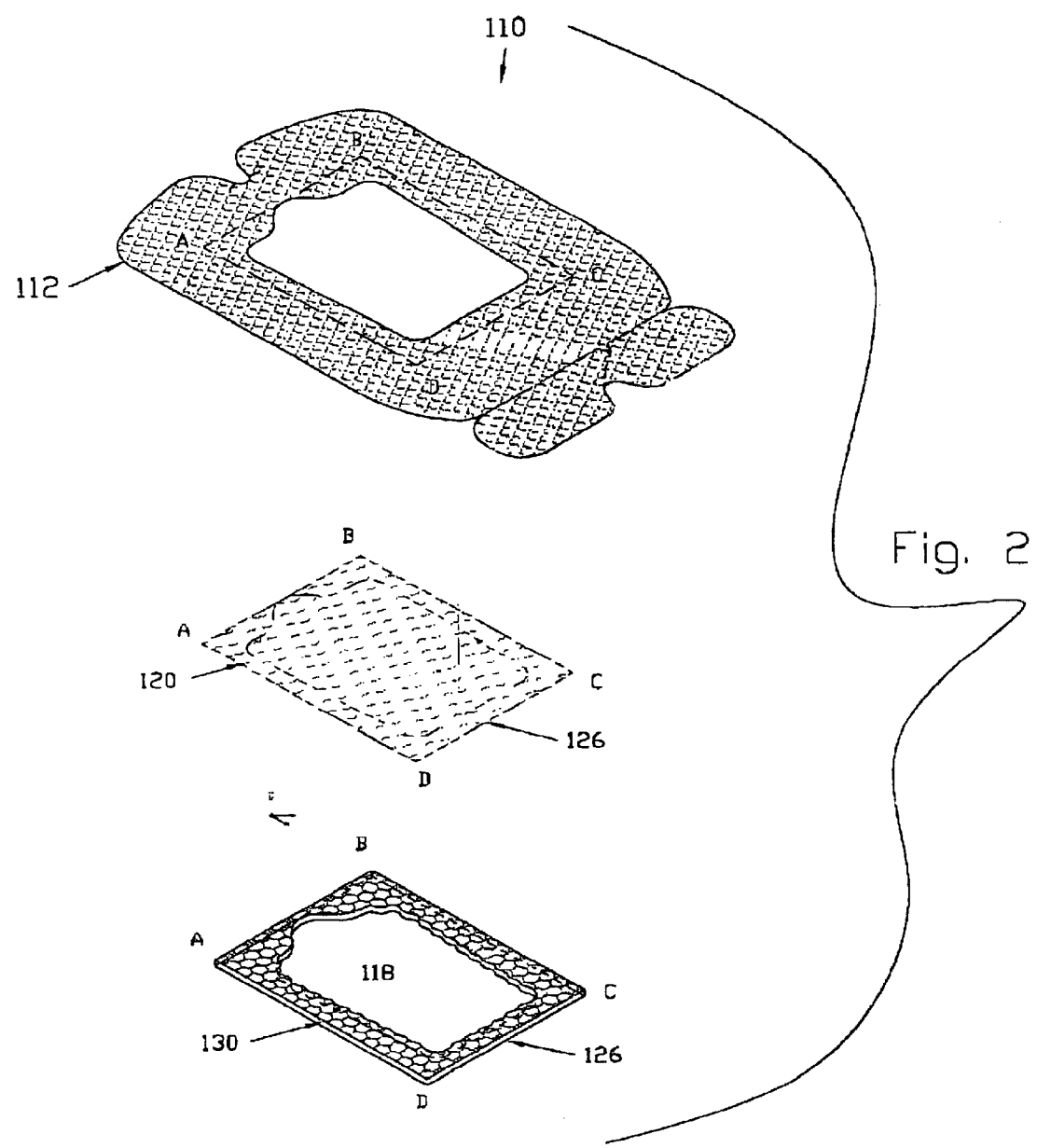
FIG. 2 is an exploded view of one embodiment of a self adherent window dressing of the invention illustrating its layered construction.

A variant of the dressing 110 is illustrated in FIG. 2 in which the absorbent fiber layer 130 shares the same outer periphery shape and size of the transparent film layer 120. In this embodiment the absorbent fiber layer 130 which is void of adhesive is held proximal to the skin by the adhesive transparent film layer 120 in the central opening 118 and continually adjoining the skin beyond the absorbent fiber layer 130 by the adhesive fabric tape layer 112 extending beyond the shared outer periphery 126 of the absorbent fiber and adhesive film layers.

Figure 3:
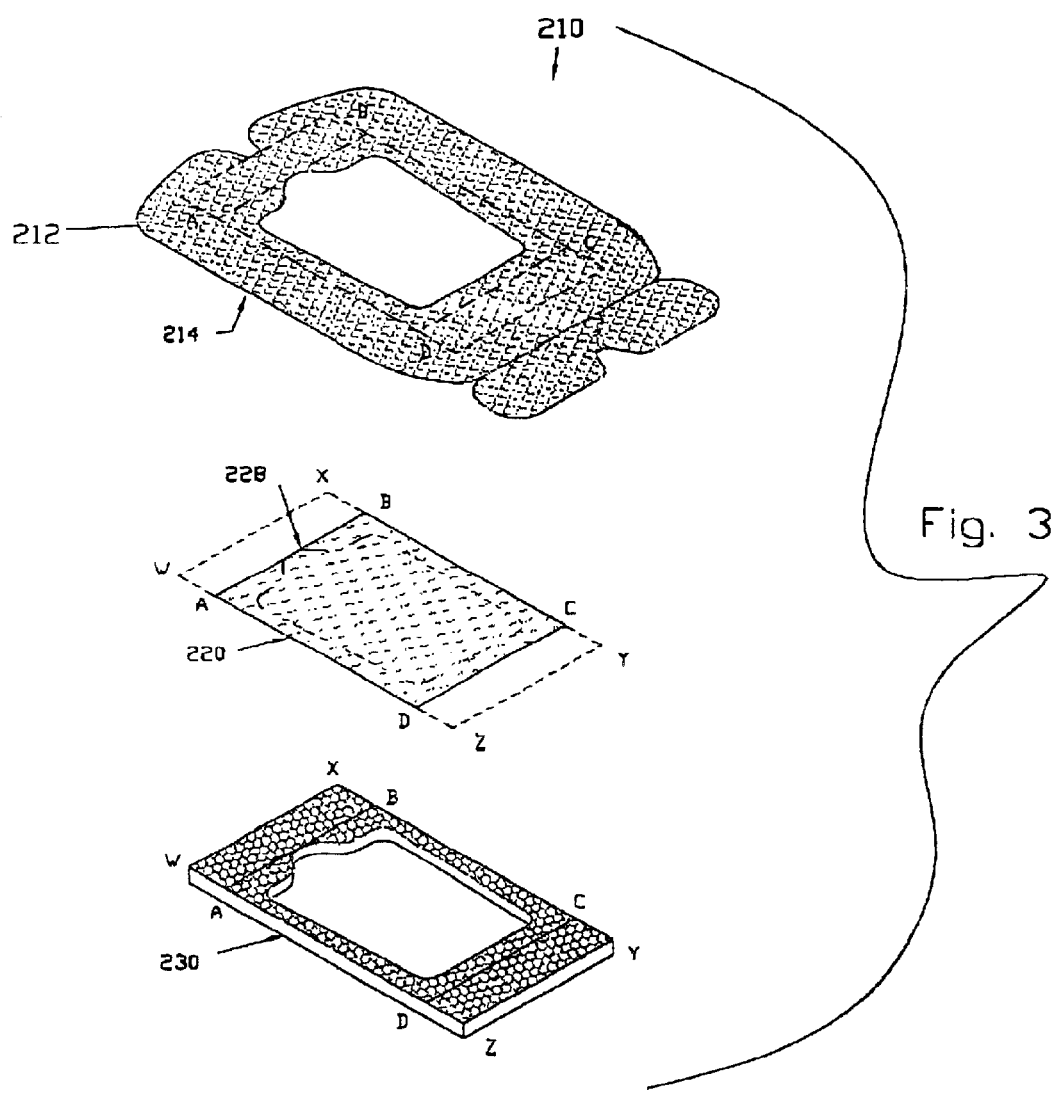
FIG. 3 is an exploded view of another embodiment of the self adherent window dressing of the invention illustrating its layered construction.

FIG. 3 illustrates another variant of the dressing 210 of FIG. 1 wherein the absorbent fiber layer 230 is unequal in size to the transparent film layer 220. Herein, the absorbent fiber layer 230 extends beyond at least one edge 228 of the film layer concurrently contacting and adhering to the adhesive side 214 of the larger adhesive fabric tape layer 212.

Figure 4:
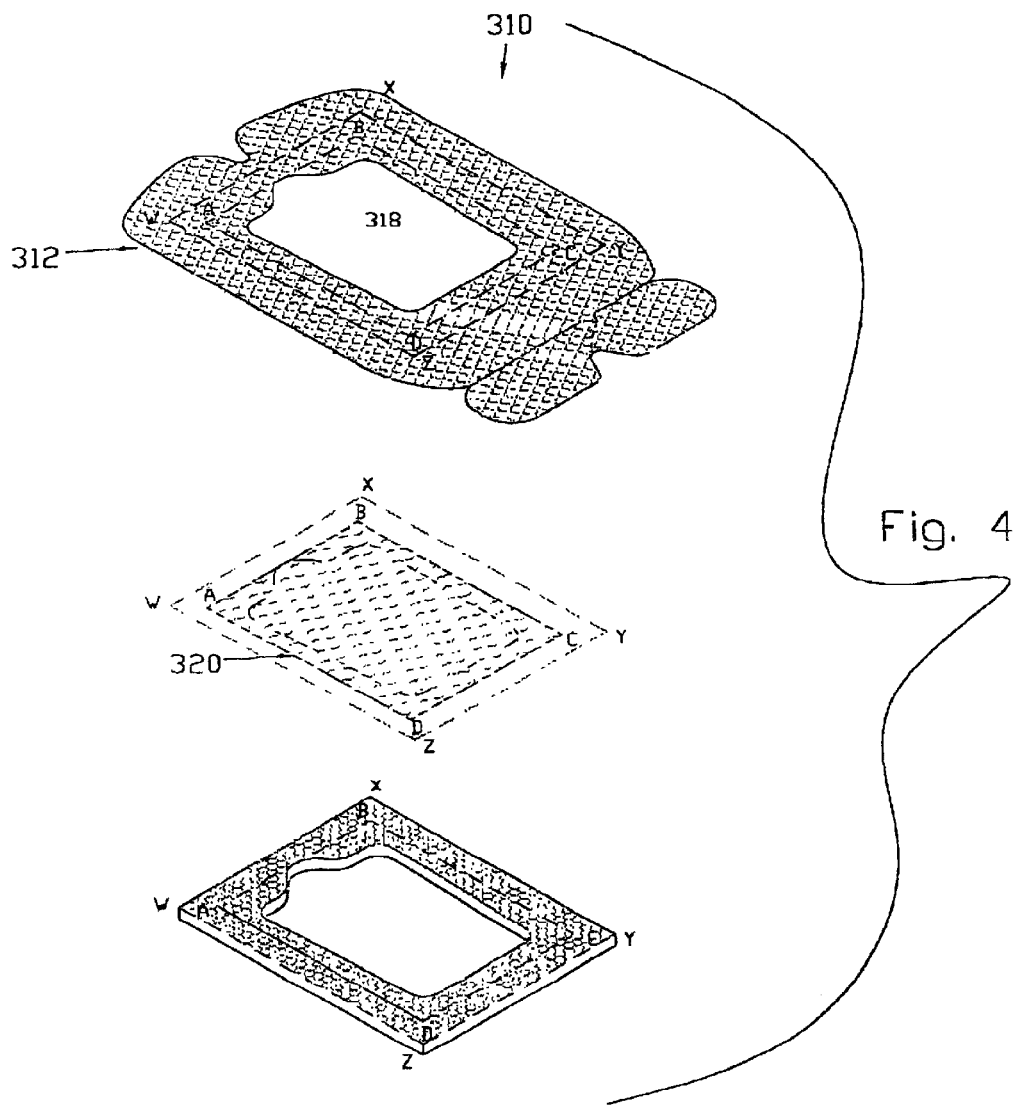
FIG. 4 is an exploded view of yet another embodiment of the self adherent window dressing of the invention illustrating its layered construction.

FIG. 4 illustrates yet another variant of the dressing 310 wherein a semipermeable transparent film layer 320 void of adhesive closes the opening 318 in the fabric tape layer 312 and has a periphery greater than a periphery of the opening 318 and less than a periphery of the fabric tape layer 312.

Figure 5:
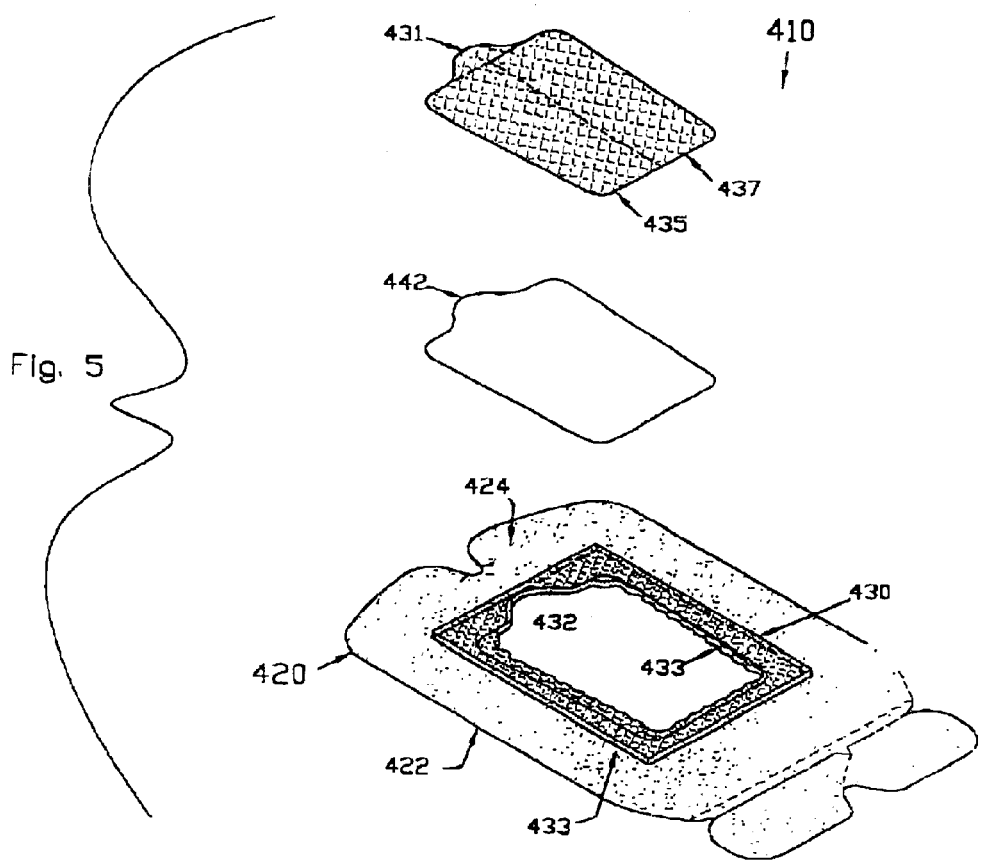
FIGS. 5 and 6 are exploded views of another embodiment of the self adherent window dressing illustrating a two layer construction wherein an absorbent fiber layer is adhered on top of a transparent film layer.
Figure 6:
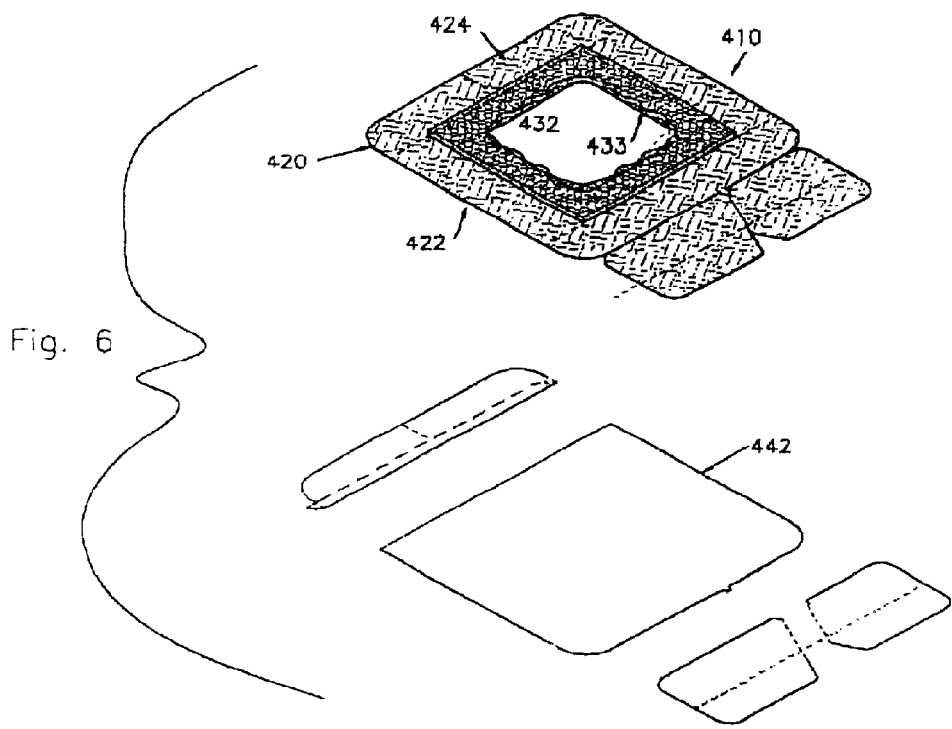

Another embodiment of the self adherent dermal wound dressing 410 is illustrated in FIGS. 5 and 6. This embodiment comprises a semipermeable transparent polyurethane film layer 420, having an adhesive skin adhering side 422 and an opposite non-adhesive side 424, and an absorbent fiber layer 430 having an opening 432 therein to allow viewing through the opening. The absorbent fiber layer 430 has an adhesive side 433. The adhesive side 433 of the absorbent fiber layer 430 is adhered to the non-adhesive (top) side 424 of the transparent film layer 420 (away from the skin) to allow gaseous moisture vapor to be mitigated from the skin surface through the film layer 420 to the surrounding ambient atmosphere. Herein the opening 432 in the absorbent fiber layer 430 may have a scalloped or curved edge 433 to increase wicking of gaseous and liquid moisture.

With further reference to FIG. 6 a release backing 442 of known construction is illustrated onto which the skin adhering surfaces of window dressings 10, 110, 210, 310 and 410 are disposed for packaging, shipping, handling, etc. prior to use on a patient.

In yet another embodiment of the self adherent dermal wound dressing 410, the absorbent fiber layer 430 having an opening 432 therein to allow viewing therethrough; the central cut portion 431 of the absorbent fiber layer 430 is typically removed and discarded in the manufacturing process. One embodiment of the current invention allows this removable central cut portion 431 of the otherwise discarded absorbent fiber layer 430 to remain adhered to the protective release backing 442 on which it is supplied. The removable central cut portion 431 is held in place attached only at the periphery of the opening 432 by the end user and allows for the viewing through the opening 432. The removable central cut portion 431 of absorbent fiber layer 430 is protected on the adhesive side 433 by a release backing 442 generally corresponding in size and shape to the removable central cut portion 431 of the absorbent fiber layer and is therefor valuable as a portion of absorbent fiber layer 430. This removable central cut portion 431 of absorbent fiber layer 430 may be subdivided into multiple smaller portions 435 and 437 of useful absorbent fiber layer by the same manufacturing process of cutting the opening area 432 that would otherwise cut through, remove and discard the central cut portion 431 in the process of manufacturing. In this embodiment the removable central cut portion 431 is reclaimed for use as an adjunct and ancillary portion of absorbent fiber layer 430, or multiple smaller portions 435 and 437 of absorbent fiber strips by subdivision of the fiber layer 430 making it useful for further use with the dressing 410.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A self adherent dermal wound window dressing for the protection of an indwelling catheter access site, and which provides the simultaneous absorption and continuous mitigation of moisture vapor, visualization of the skin/cannula exit point and mechanical securement of the indwelling catheter, the window dressing comprising:

a fabric tape layer having an adhesive skin adhering side and an opposite non-adhesive side; said fabric tape layer having an opening therein to allow viewing therethrough;

a semipermeable transparent film layer closing said opening in said fabric tape layer and having an adhesive skin adhering side and an opposite non-adhesive side; said film layer non-adhesive side being adhered on the adhesive side of said fabric layer around said opening such that said fabric layer extends beyond the periphery of said transparent film layer; and an absorbent fiber layer having an opening generally corresponding to said opening in said fabric tape layer, said fiber layer being mounted on the adhesive skin adhering side of said transparent film layer such that said openings in said absorbent fiber and fabric tape layers are in alignment and said transparent film layer extends beyond the periphery of said absorbent fiber layer.

2. A self adherent dermal wound window dressing for the protection of an indwelling catheter access site, and which provides the simultaneous absorption and continuous mitigation of moisture vapor, visualization of the skin/cannula exit point and mechanical securement of the indwelling catheter, the window dressing comprising:

a fabric tape layer having an adhesive skin adhering side and an opposite non-adhesive side; said fabric tape layer having an opening therein to allow viewing therethrough;

a semipermeable transparent film layer closing said opening in said fabric tape layer and having an adhesive skin adhering side and an opposite non-adhesive side; said film layer non-adhesive side being adhered on the adhesive side of said fabric layer around said opening such that said fabric layer extends beyond the periphery of said transparent film layer; and an absorbent fiber layer having an opening generally corresponding to said opening in said fabric tape layer, said fiber layer being mounted on the adhesive skin adhering side of said transparent film layer such that said openings in said absorbent fiber and fabric tape layers are in alignment, and said absorbent fiber layer shares the same outer periphery shape and size of said transparent film layer; the absorbent fiber layer void of adhesive is thereby held proximal to the skin by the said adhesive transparent film layer in the central opening and continually adjoining the skin beyond the said absorbent fiber layer by the said adhesive fabric tape layer extending beyond the shared outer periphery of the said absorbent fiber and adhesive film layers.

3. A self adherent dermal wound window dressing for the protection of an indwelling catheter access site, and which provides the simultaneous absorption and continuous mitigation of moisture vapor, visualization of the skin/cannula exit point and mechanical securement of the indwelling catheter, the window dressing comprising:

a fabric tape layer having an adhesive skin adhering side and an opposite non-adhesive side; said fabric tape layer having an opening therein to allow viewing therethrough;

a semipermeable transparent film layer closing said opening in said fabric tape layer and having an adhesive skin adhering side and an opposite non-adhesive side; said film layer non-adhesive side being adhered on the adhesive side of said fabric layer around said opening such that said fabric layer extends beyond the periphery of said transparent film layer; and an absorbent fiber layer having an opening generally corresponding to said opening in said fabric tape layer, said fiber layer being mounted on the adhesive skin adhering side of said transparent film layer such that said openings in said absorbent fiber and fabric tape layers are in alignment, and the outer perimeter of said absorbent fiber layer is unequal in size to said transparent adhesive film layer and extends beyond at least one edge of said film layer concurrently contacting and adhering to the adhesive side of the larger said adhesive fabric tape layer;

the absorbent fiber layer void of adhesive is thereby held proximal to the skin by the said adhesive transparent film layer in the central opening, and by the larger said adhesive fabric tape layer continually adjoining the skin beyond the said fiber layer concurrently contacting and adhering to the said fiber layer extending beyond at least one edge of said transparent film layer.

4. A self adherent dermal wound window dressing for the protection of an indwelling catheter access site, and which provides the simultaneous absorption and continuous mitigation of moisture vapor, visualization of the skin/cannula exit point and mechanical Securement of the indwelling catheter, the window dressing comprising:

a fabric tape layer having an adhesive side and an opposite non-adhesive side; said fabric tape layer having an opening therein to allow viewing therethrough;

a semipermeable transparent film layer void of adhesive closing said opening in said fabric tape layer and having a periphery greater than a periphery of said opening and less that a periphery of said fabric tape layer; and an absorbent fiber layer void of an adhesive having an opening generally corresponding to said opening in said fabric tape layer, said fiber layer being mounted on the adhesive side of said fabric tape layer such that said openings in said absorbent fiber and fabric tape layers are in alignment and said absorbent fiber layer extends beyond the periphery of said transparent film layer and said fabric tape layer extends beyond the periphery of said absorbent fiber layer.

5. The self adherent window dressing as in any of claims 1–4 wherein said fabric tape layer comprises a nonwoven polyester material.

6. The self adherent window dressing as in any of claims 1–4 wherein said tape non-adhesive side has a textural surface.

7. The self adherent window dressing as in any of claims 1–4 wherein said tape layer non-adhesive side includes a water repellant coating.

8. The self adherent window dressing as in any of claims 1–4 wherein said transparent film layer comprises a semipermeable polyurethane material.

9. The self adherent window dressing as in any of claims 1–4 wherein said absorbent fiber layer has a scalloped edge around its said opening therein.

10. The self adherent window dressing as in any of claims 1–4 including at least one removable central cut portion of one of a fabric tape layer and absorbent fiber layer held in place and attached only at the periphery of the opening and capable of being removed easily from the opening by the end user to allow viewing through the opening; the removable central cut portion being protected on the adhesive side by a release backing generally corresponding in size and shape to the removable central cut portion and being valuable as a portion of fabric tape or absorbent fiber layer.

11. The self absorbent window dressing as in any of claims 1–4 including a label portion removably mounted along an outside edge of the dressing.

* * * * *